(12) United States Patent
Harrer et al.

(10) Patent No.: US 9,714,933 B2
(45) Date of Patent: Jul. 25, 2017

(54) MICRO-DROPLET FLUIDIC CELL FOR FAST IONIC CURRENT DETECTION USING NANOPORES

(71) Applicant: International Business Machines Corporation, Armonk, NY (US)

(72) Inventors: Stefan Harrer, New York, NY (US); Young H. Kwark, Chappaqua, NY (US); Stanislav Polonsky, Putnam Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 398 days.

(21) Appl. No.: 14/165,875

(22) Filed: Jan. 28, 2014

(65) Prior Publication Data

US 2015/0209779 A1 Jul. 30, 2015

(51) Int. Cl.
*G01N 33/487* (2006.01)

(52) U.S. Cl.
CPC . *G01N 33/48728* (2013.01); *G01N 33/48721* (2013.01)

(58) Field of Classification Search
CPC ....... G01N 33/48721; G01N 33/48728; G01N 2035/00425; G01N 2035/1037
See application file for complete search history.

(56) References Cited

U.S. PATENT DOCUMENTS

| | | | |
|---|---|---|---|
| 6,232,129 B1 * | 5/2001 | Wiktor | B01L 3/021 422/417 |
| 7,226,862 B2 | 6/2007 | Staehler et al. | |
| 7,777,505 B2 | 8/2010 | White et al. | |
| 7,849,581 B2 | 12/2010 | White et al. | |
| 7,900,519 B2 | 3/2011 | Chandrasekaran | |
| 8,338,049 B2 | 12/2012 | Spoto et al. | |
| 2002/0190839 A1* | 12/2002 | Padmanabhan | G01F 1/6842 338/13 |
| 2005/0102721 A1* | 5/2005 | Barth | G01N 33/48721 438/108 |
| 2007/0020146 A1* | 1/2007 | Young | G01N 33/48721 422/82.01 |
| 2007/0092432 A1* | 4/2007 | Prud'Homme | C01B 31/043 423/448 |
| 2007/0190542 A1* | 8/2007 | Ling | C12Q 1/6816 435/6.11 |
| 2007/0202495 A1* | 8/2007 | Mayer | G01N 33/48721 435/5 |
| 2007/0207064 A1* | 9/2007 | Kohara | B01F 7/00258 422/400 |

(Continued)

FOREIGN PATENT DOCUMENTS

CN 102745645 A 10/2012
WO 2006015306 A2 2/2006

*Primary Examiner* — Jill Warden
*Assistant Examiner* — Matthew Krcha
(74) *Attorney, Agent, or Firm* — Cantor Colburn LLP; Louis Percello

(57) ABSTRACT

A micro-droplet fluidic cell includes a membrane structure having a nanopore, a hydrophobic material disposed onto a portion of the membrane structure, and an analyte solution traversing the membrane structure and forming a micro-droplet on a first surface of the membrane structure. Also disclosed are methods for fast ionic current detection using the micro-droplet fluidic cell.

14 Claims, 5 Drawing Sheets

(56) References Cited

U.S. PATENT DOCUMENTS

| | | | |
|---|---|---|---|
| 2009/0194429 A1* | 8/2009 | Hibbs | G01N 33/48728 205/778 |
| 2011/0174629 A1* | 7/2011 | Bouchet | G01N 33/48721 205/131 |
| 2012/0021204 A1* | 1/2012 | Pei | B81C 1/00087 428/314.2 |
| 2012/0071330 A1* | 3/2012 | Kokoris | C12Q 1/6825 506/4 |
| 2012/0145549 A1* | 6/2012 | Cho | G01N 33/48721 204/603 |
| 2012/0228779 A1 | 9/2012 | King, Jr. et al. | |
| 2013/0026038 A1 | 1/2013 | Oliver | |
| 2013/0264206 A1* | 10/2013 | Eom | C12Q 1/68 204/452 |

* cited by examiner

MICRO-DROPLET FLUIDIC CELL FOR FAST IONIC CURRENT DETECTION USING NANOPORES

BACKGROUND

The present disclosure generally relates to nanopore devices, and more specifically, to nanopore devices utilizing micro-droplets.

Measuring the ionic current flowing through a membrane nanopore as the ionic current is modulated by a transiting biological molecule can reveal useful information about the transiting species. These analytical methods have varied applications, ranging from biological research to diagnostic capabilities in a health care setting.

Conventional techniques for measuring this current involve using a "fluidic cell," which includes a multi-layer membrane comprising an aperture, or nanopore, providing a fluidic connection between two opposing reservoirs containing an analyte and a buffer or ionic solution. Further, these conventional fluidic cells have a perimeter seal, e.g., "o-rings," that occupy a relatively large volume due to the manual operations needed to assemble the cell. This large volume, which can be several cubic millimeters, also requires at least several microliters of costly analyte solution.

SUMMARY

In one embodiment of the present disclosure, a micro-droplet fluidic cell comprises a membrane structure comprising a nanopore; a hydrophobic material disposed onto a portion of the membrane structure; and an analyte solution traversing the membrane structure and forming a micro-droplet on a first surface of the membrane structure.

In another embodiment, a micro-droplet fluidic cell comprises a membrane structure having a first surface and a second surface; a hydrophobic material disposed onto a portion of the first surface and the second surface of the membrane structure; and an analyte solution disposed onto the first surface of the membrane structure. The membrane structure comprises an etched membrane support comprising an aperture and a thin membrane comprising a nanopore. The nanopore is aligned with the aperture, and the analyte solution traverses the membrane structure and forms a micro-droplet.

Yet in another embodiment, a method for fast ionic current detection comprises forming a membrane structure having a first surface and a second surface; disposing a hydrophobic material onto a portion of the first and second surfaces of the membrane structure; and disposing a drop of an analyte solution onto the membrane structure. The membrane structure comprises an etched membrane support comprising an aperture and a thin membrane comprising a nanopore. The nanopore is aligned with the aperture, and the analyte solution forms a first micro-droplet on the first surface and traverses the membrane structure to form a second micro-droplet on the second surface.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
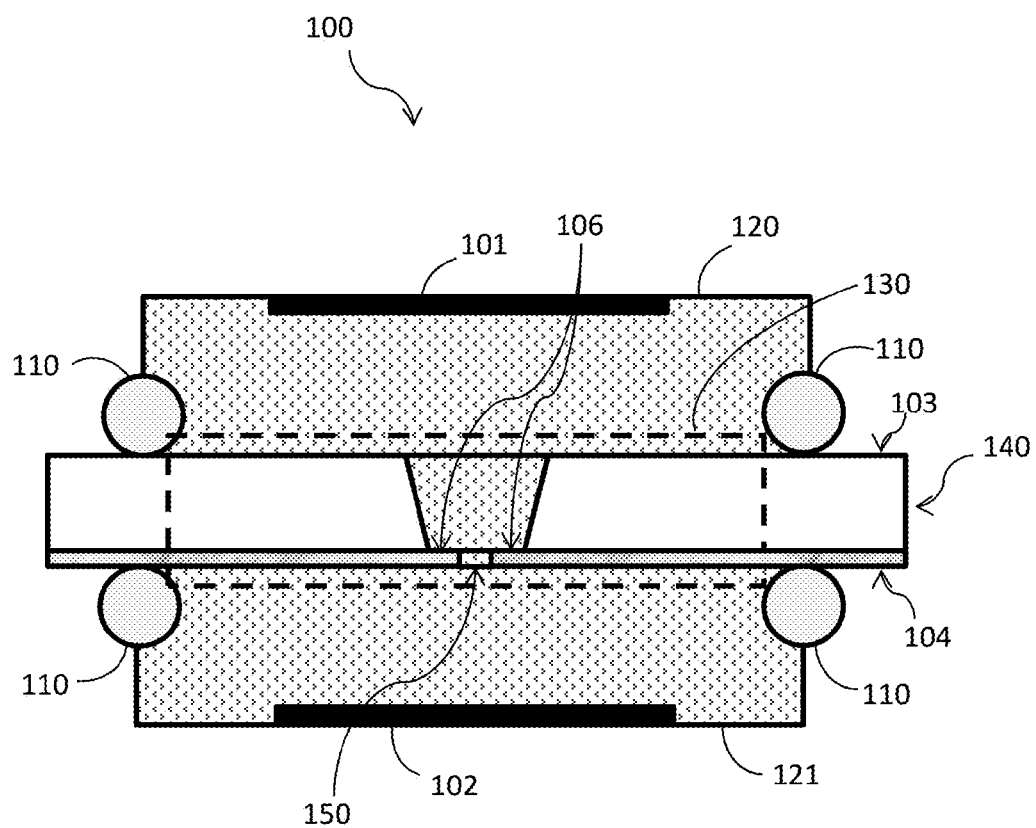
FIG. 1 illustrates a partially cut-away side view of a conventional fluidic cell.

Disclosed herein are a micro-droplet fluidic cell, methods of making the fluidic cells, and methods of fast ionic current detection using the fluidic cells. In one embodiment, a micro-droplet fluidic cell comprises a membrane structure having a nanopore, a hydrophobic material disposed onto a portion of the membrane structure, and an analyte solution traversing the membrane structure and forming a micro-droplet on a first surface of the membrane structure.

In another embodiment, a micro-droplet fluidic cell comprises a membrane structure having a first surface and a second surface, with the membrane structure comprising an etched membrane support comprising an aperture and a thin membrane having a nanopore. Further, the nanopore is aligned with the aperture, a hydrophobic material is disposed onto a portion of the first and second surfaces of the membrane structure, and an analyte solution is disposed onto the first surface of the membrane structure. The analyte solution traverses the membrane structure and forms a micro-droplet.

Yet in another embodiment, a method for fast ionic current detection comprises forming a membrane structure having a first surface and a second surface and disposing a hydrophobic material onto a portion of the first and second surfaces of the membrane structure. The membrane structure comprises an etched membrane support comprising an aperture, a thin membrane comprising a nanopore, and the nanopore is aligned with the aperture. A drop of an analyte solution is disposed onto the membrane structure, and the analyte solution forms a first micro-droplet on the first surface. The analyte solution traverses the membrane structure to form a second micro-droplet on the second surface.

As used herein, the term "parasitic capacitance" means unavoidable capacitance that exists between the parts of a fluidic cell because of their proximity to each other. For the relatively low frequencies involved with the nanopore structure, the capacitance can be measured using commercially available LCR meters (electronic test equipment used to measure the inductance (L), capacitance (C), and resistance (R) of a component) or can be inferred from an impedance measurement using, e.g., lock-in amplifiers.

As used herein, the term "hydrophobic" means substantially immiscible in water.

As used herein, the terms "conductive" or "conducting" mean having the property of being able to conduct electric current.

As used herein, the term "analyte" refers to a compound, molecule, substance, or chemical constituent that is undergoing analysis or sought to be detected. It is not intended that the present disclosure be limited to a particular analyte. Representative analytes include ions, saccharides, proteins, nucleic acids, cells, and cellular organelles, e.g., exosomes.

Conventional fluidic cells often have several disadvantages. First, the large volume occupied by the o-ring perimeter seals, which can be several cubic millimeters, uses at least several microliters of costly analyte solution. Another, disadvantage of the conventional fluidic cell arises from the large parasitic capacitance that results from the combination of large wetted surface area coupled with the thin membrane in which the transiting nanopore resides. This parasitic capacitance shunts the ionic current signal. The parasitic capacitance, which can be as large as a nanoFarad (nF), results in a high noise floor (kTC noise for a trans impedance amplifier) and a limited bandwidth for ionic current measurements. The restricted bandwidth and decreased sensitivity vitiate measurement efficiency, resulting in slower throughput or conversely a higher error rate.

Thus, conventional fluidic cells suffer from a large ratio of total wetted area defined by the o-rings to functional area of the nanopore. In some cases, this ratio can be as large as 1,000,000,000:1. The present disclosure provides a fluidic cell that both reduces parasitic capacitance and allows for use of smaller volumes of analyte solutions.

Turning now to the figures, FIG. 1 illustrates a partially cut-away side view of an exemplary embodiment of a conventional fluidic cell 100. The fluidic cell 100 includes a membrane structure 140 having a first surface 103 and an opposing second surface 104. The first and second surfaces, 103 and 104 respectively, juxtapose a first fluidic reservoir 120 and a second fluidic reservoir 121. The membrane structure 140 may include multiple layers and defines a nanopore (aperture) 150 extending through the membrane structure 140 from the first surface 103 to the second surface 104. The nanopore 150 has a minimal diameter, which is tailored to the specific application.

Seal portions 110 are sealingly engaged between the first and second surfaces 103 and 104 of the membrane structure 140 and the first and second fluidic reservoirs 120 and 121. The first and second fluidic reservoirs 120 and 121 are in fluid communication via the nanopore 150. The fluidic cell 100 further comprises a first electrode 101 and a second electrode 102. The seal portions 110 may include, for example, o-ring gaskets made of, for example, Viton.

The first and second fluidic reservoirs 120 and 121 are filled with a conductive solution that stabilizes the biological molecules of interest and provides a conductive path from the first fluidic reservoir 120 through the nanopore 150 to the second fluidic reservoir 121. The conductive solution generally includes a buffer, charged ions, and the analyte of interest.

In operation, a voltage is applied across the membrane structure 140 that drives an ionic current that can only traverse the nanopore 150. The ionic current is modulated as the analyte traverses through the nanopore 150. When the analyte is charged, the electric field across the nanopore 150 affects movement of the analyte. When the analyte is neutral, the flow of charged ions through the nanopore 150 can exert a viscous drag to transport the analyte.

The modulation amplitude of the ionic currents may be on the order of tenths of a picoAmpere (pA) to several hundred pA, which is a weak signal. Thermal noise sets an ultimate limit to the noise floor contributed by the electronic amplifier that is used to amplify this weak signal. This noise power spectral density is proportional to the square of the parasitic capacitance (cf: Solid-State Nanopores Integrated with Low-Noise Preamplifiers for High-Bandwidth DNA Analysis, Rosenstein et al., 2100 IEEE/NIH Life Science Systems and Applications Workshop, pg 59) created by the membrane structure 140 separating the first and second fluidic reservoirs 120 and 121. Hence, this parasitic capacitance is proportional to the wetted area 130 of the membrane structure 140 and inversely proportional to the thickness of the membrane structure 140. An additional contribution comes from the thinned region 106 of the membrane. The membrane structure 140 is thinned (thinned region 106) to produce narrow diameter nanopores 150 with reasonable aspect ratios. Although the thinned region 106 area is small, the absolute thinness necessitated by fabrication of the small diameter nanopore 150 can result in a significant contribution to parasitic capacitance.

While decreasing the measurement bandwidth can decrease the noise, small bandwidths result in inordinately long measurement times for assessing analyte transit through the nanopore 150, assuming that the transiting speed of the species of interest through the nanopore 150 can be controlled, e.g., by altering the electrical bias across the pore. However, this range of control may be limited, which will result in loss of higher frequency information and a reduction in signal amplitude. Hence, a poorer signal-to-noise ratio results. Although applying lower voltages can increase this transit time, smaller bandwidths may not permit measurements consistent with reasonable transit times. In any case, slower measurements are not desired, especially in applications where fast analyte identification is desired.

Thus, the disclosed micro-fluidic cell avoids the disadvantages of the conventional cells by utilizing micro-droplets of analyte. To form the micro-droplets, the nanopore and the immediate surrounding regions must be hydrophilic, whereas the outer remote regions are hydrophobic to contain the spread of the micro-droplets. These micro-droplets are constrained by surface wetting and surface tension forces in a way that self-aligns with the wetted volume of the nanopore and the detection electrodes. This alignment reduces the parasitic capacitance by several orders of magnitude. The commensurate reduction in required analyte volume reduces the costs associated with sample preparation. The smaller analyte volume makes temperature control of the analyte feasible with reasonable power dissipation.

Figure 2:
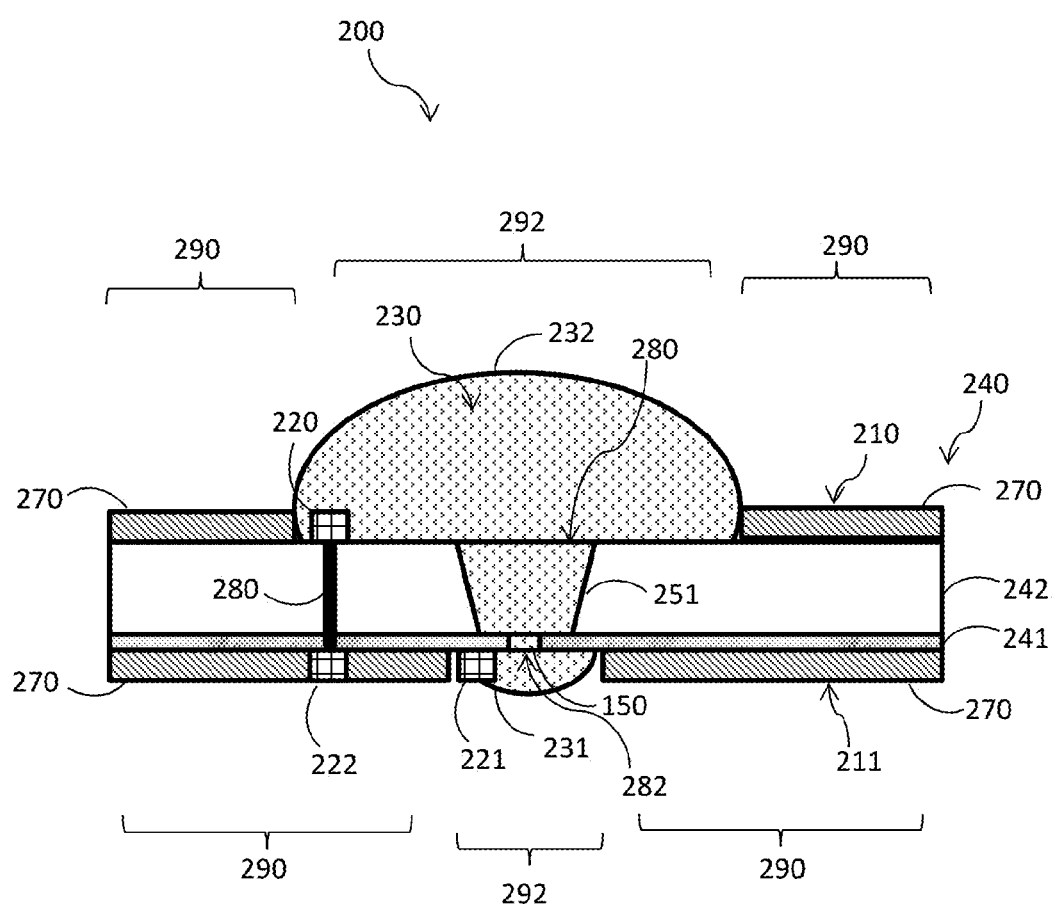
FIG. 2 illustrates a partially cut-away side view of an exemplary embodiment of a micro-droplet fluidic cell utilizing Through Silicon Via (TSV) technology.

FIGS. 2-4 illustrate exemplary embodiments of micro-droplet fluidic cells. In all embodiments, a membrane structure 240 includes a thin membrane 241 and an etched membrane support 242. The thin membrane 241 defining a nanopore 150 is disposed onto the etched membrane support 242 that defines a small aperture 251 abutting and in line with the nanopore 150. Regions of the aperture 251 should be hydrophilic. An analyte solution 230 traverses the membrane structure 240 and forms a first micro-droplet 232 on the first surface 210 of the membrane structure 240 and a second micro-droplet 231 on the second surface 211 of the membrane structure 240.

The etched membrane support 242 may be fabricated from substrates such as chips, disks, blocks, plates and the like. Such substrates may be made from a variety of materials, including, but not limited to silicon, including silicon oxide, silicon nitride, glass, ceramic, germanium, polymers (e.g., polystyrene), gallium arsenide, or any combination thereof. The etched membrane support 242 may have multiple layers. The thickness of the substrate, as well as the thickness of the individual layers within a multi-layer substrate, can generally vary. Thus, the particular thickness of the etched membrane support 242 is not intended to be limited.

Etching, for example with KOH when using silicon as the substrate material, is used to create the aperture 251 within the etched membrane support 242. The etching method is not intended to be limited and can be accomplished by any method known in the art. Non-limiting exemplary etching methods include Reactive Ion Etching (RIE) and wet etching, e.g. using a TMAH solution.

The aperture 251 size and diameter is not intended to be limited and may be tailored to the desired application. The aperture diameter may be about 100 micrometers to about 100 nanometers.

A thin membrane 241 is disposed onto the membrane support 242. The thin membrane 241 may be fabricated using any suitable fabrication process, including but not limited to, chemical vapor deposition (CVD) methods, plasma enhanced chemical vapor deposition (PECVD) methods, lithographic patterning and etching methods, and epitaxial growth processes. The thin membrane 241 may be fabricated from any of the above materials or combination of materials used for the etched membrane support 242.

The nanopore 150 is then fabricated through the thin membrane 241 by any suitable process, including but not limited to, electron beam drilling or ion beam drilling. The diameter of the nanopore 150 generally varies but narrows down to a dimension desirable for the intended application. The particular size is not intended to be limited. The nanopore diameter may be from about 1 nm to 900 nm. In other embodiments, the nanopore diameter is from about 20 nm to 100 nm. Still in other embodiments, the nanopore diameter is from about 100 nm to 500 nm.

FIG. 2 shows an exemplary embodiment of a micro-droplet fluidic cell 200 utilizing Through Silicon Via (TSV) technology. Micro-droplet fluidic cell 200 includes a membrane structure 240 having a first surface 210 and a second surface 211. The membrane structure 240 includes an etched membrane support 242 having an aperture 251 and a thin membrane 241 having a nanopore 150. The first and second surfaces 210 and 211 define first and second openings 280 and 282 on opposing sides of the membrane structure 240. The aperture 251 is aligned with the nanopore 150.

A hydrophobic material 270 is disposed onto a portion of the first and second surfaces 210 and 211 of the membrane structure 240. The hydrophobic material 270 may be disposed onto lateral portions 290 of the first and second surfaces 210 and 211. The medial portions 292 of the membrane structure 240, which are in contact with the first and second openings 280 and 282, do not include the hydrophobic material 270. Thus, the medial portions 292 are hydrophilic, relative to the lateral portions 290 having the hydrophobic material 270 disposed thereon.

The hydrophobic material 270 may be selected based on the intended application and applied as a layer or a coating. The hydrophobic material 270 is not intended to be limited. Suitable hydrophobic materials include, but are not limited to, hydrophobic polymeric materials, such as poly(tetrafluorethene) (PTFE), polypropylene (PP), polyamides, polyvinylidene, polyethylene, polysiloxanes, silicone, rubber, polyglactin, lyophilized dura mater, or any combination thereof.

A first electrode 220 and a second electrode 221 are patterned onto opposing surfaces of the etched membrane support 240, in particular onto the relatively hydrophilic medial portions 292. Thus, the first and second electrodes 220 and 221 directly contact the analyte solution 230 on opposing sides of the etched membrane support 240.

The TSV 280, or microvia, traverses the etched membrane support 240 and the thin membrane 241 and may be a hole filled with, for example, copper or polysilicon. Alternatively, the TSV 280 may be a metal wire. However, the TSV 280 is not intended to be limited and may be any structure or material known in the art suitable for connecting the first and second electrodes 220 and 221 on opposing sides of the membrane structure 240. Optionally, a third electrode 222 is patterned onto the lower portion of the TSV 280 on the thin membrane 241, opposing the first electrode 220. Both second and third electrodes 221 and 222 may be accessed on the bottom surface of thin membrane 241, which allows integration with planar circuitry in the vicinity (not shown).

When a droplet of analyte solution 230 is dispensed onto the membrane structure 240, the surface tension and the repellant nature of the hydrophobic material 270 define a first micro-droplet 232. The hydrophobic material 270 and the relatively hydrophilic medial portions 292 limit the total volume of analyte solution 230 that remains on the membrane structure 240. Control of the total dispensed volume of analyte solution 230 does not need to be tightly controlled because excess volume is readily removed upon formation of the micro-droplet 232. The analyte solution 230 traverses the aperture 251 and nanopore 150 and exits through the second opening 282, forming a second micro-droplet 231. The second electrode 221 is positioned close enough to the second opening 281 so that only a small volume of the analyte solution 230 needs to traverse the nanopore 150 to wet the second electrode 221.

The diameter of the first micro-droplet 232 generally varies and is not intended to be limited. The diameter of the first micro-droplet 232 is about 1 micrometer to about 1 millimeter (mm). In other embodiments, the diameter of the first micro-droplet 232 is about 50 micrometers to about 800 micrometers. Still in other embodiments, the diameter of the first micro-droplet 232 is about 100 micrometers to about 500 micrometers.

The diameter of the second micro-droplet 231 generally varies and is not intended to be limited. However, the second micro-droplet 231 diameter may be smaller than the first micro-droplet 232 to reduce parasitic capacitance. The diameter of the second micro-droplet 231 is about 1 micrometer to about 10 micrometers. In other embodiments, the diameter of the second micro-droplet 231 is about 3 micrometers to about 8 micrometers. Still in other embodiments, the diameter of the second micro-droplet 231 is about 2 micrometers to about 6 micrometers.

As in conventional fluidic cells, the analyte solution 230 may be transported across the nanopore 150 by applying a voltage. Additionally, the analyte solution 230 may be drawn into the nanopore 150 by applying a pressure differential across the membrane structure 240. Non-limiting examples of suitable methods for applying pressure differentials include using a conventional pump or deflecting a piezoelectric membrane that resembles those commonly found in tone generators. Hydrophilic surface treatments can be used to rely on capillary wetting of the nanopore 150.

Control and duration of the pressure differential allows for fine control of the volume of analyte solution 230 that transits through the nanopore 150 and forms the second micro-droplet 231. Controlling and decreasing the fraction of the first micro-droplet 232 volume that wets the opposing surface of the membrane structure 240 reduces parasitic capacitance, which is defined by the overlap area of the first and second micro-droplets 232 and 231 on opposing sides of the membrane structure 240. For example, compared to a conventional fluidic cell with an o-ring diameter of 100 microns (a very small o-ring), a micro-droplet fluidic cell having a second micro-droplet 231 with a one micron diameter reduces the wetted area by a factor of 10,000. When the o-ring diameter is one millimeter, the micro-droplet fluidic cell reduces the parasitic area by a factor of 1,000,000.

The micro-droplet fluidic cell 200 is but an exemplary embodiment. Other embodiments of the micro-droplet fluidic cell 200 may be used.

Figures 3A, 3B, 3C:
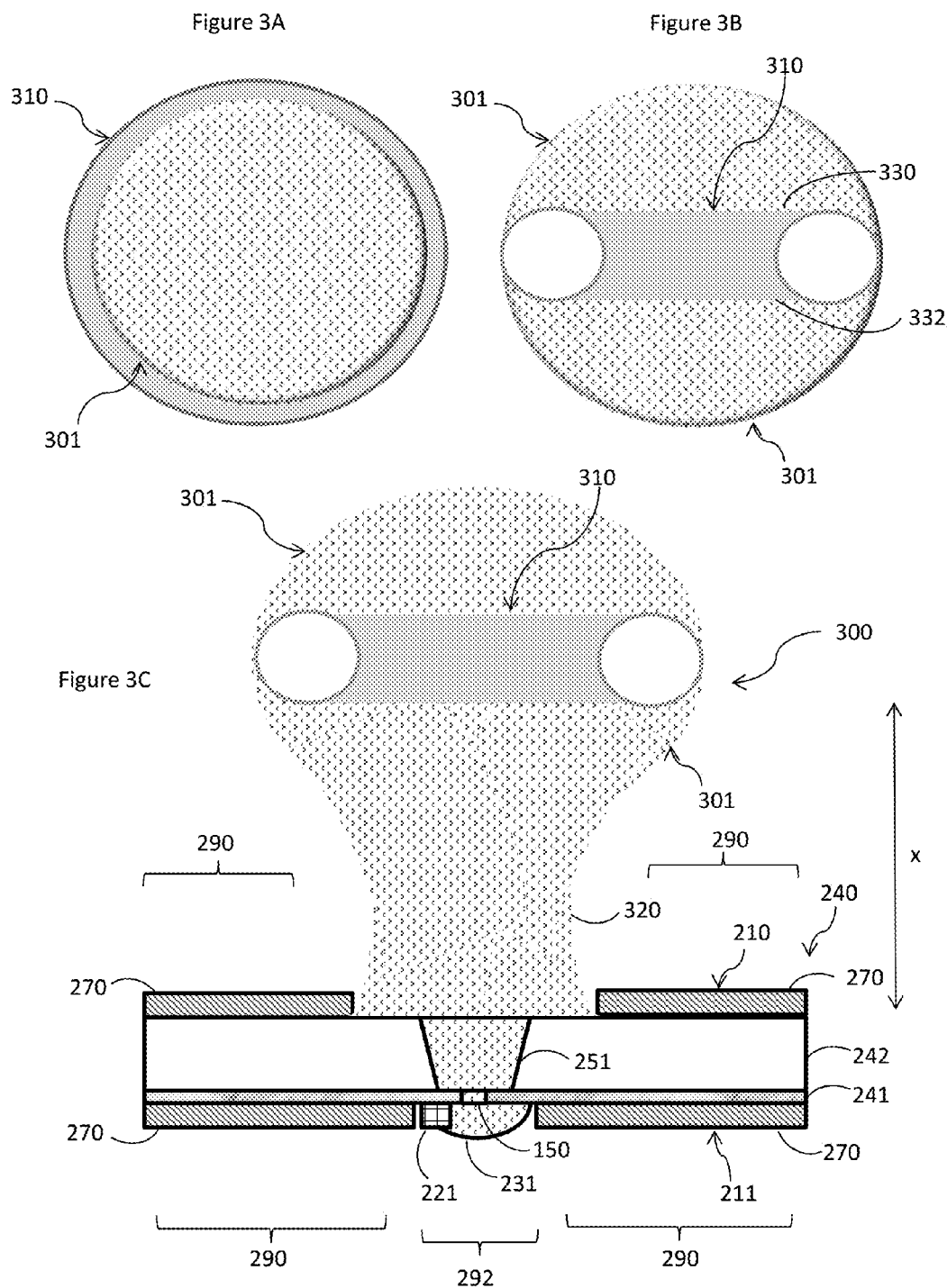
FIG. 3A illustrates a top view of an exemplary embodiment of a conductive ring.
FIG. 3B illustrates a partially cut-away side view of an exemplary embodiment of a conductive ring wetted with an analyte solution before contacting the fluidic cell.
FIG. 3C illustrates a partially cut-away side view of an exemplary embodiment of a micro-droplet fluidic cell utilizing the conductive ring of FIG. 3B.

FIGS. 3A-C illustrate exemplary embodiments of micro-droplet fluidic cells utilizing a conductive ring 310 to form the micro-droplet. FIG. 3A shows a top view of the conductive ring 310 with drop of analyte solution 230 forming a micro-droplet 301 within the conductive ring 310.

FIG. 3B shows a partially cut-away side view of the conductive ring 310 with the analyte solution 230 forming a micro-droplet 301 on the first and second portions 330 and 332 of the conductive ring 310. As shown, the initial shape of the analyte solution 230 forms a spherical micro-droplet shape 301 within the conductive ring 310.

The conductive ring 310 may be wetted to form the initial micro-droplet 301 shape by dipping the conductive ring 310 into a larger volume of analyte solution 230. Alternatively, the analyte solution 230 is dispensed into the conductive ring 310 by spraying the analyte solution 230 into the conductive ring 310. When analyte solution 230 volumes are limited, a micro-pipette can be used to dispense the analyte solution 230 into the conductive ring 310.

The conductive ring 310 may be a loop. The conductive ring material is not intended to be limited and may be any conductive material, for example a metal or plated plastic. Non-limiting examples of suitable materials for the conductive ring 310 include copper, aluminum, gold, silver, nickel, carbon, silver ink, semiconductor materials, or any combination thereof.

The conductive ring 310 may be suitably coated or treated to allow the analyte solution 230 to wet the conductive ring 310. The coating or surface treatment should also provide a suitable low-impedance electrochemical interface to the analyte solution 230.

FIG. 3C shows an exemplary embodiment of a micro-droplet fluidic cell 300, with the conductive ring 310 having the micro-droplet 301 contacting the membrane structure 240. As described in FIG. 2, the membrane structure 240 includes an etched membrane support 242 having an aperture 251 and a thin membrane 241 having a nanopore 150 aligned with the aperture 251. A hydrophobic material 270 is disposed onto lateral portions 290 of the membrane structure 240. However, in contrast to micro-droplet fluidic cell 200 in FIG. 2, the membrane structure 240 does not use TSV 280 technology. Only one electrode, the second electrode 221, is used. The conductive ring 310 functions as the opposing electrode (substituting for the first electrode 220 in FIG. 2).

In operation, the conductive ring 310 with micro-droplet 301 is brought into contact with the membrane structure 240 in proximity to the first opening 280. Then, the conductive ring 310 is slightly raised after the micro-droplet 301 wets the membrane structure 240. As the conductive ring 310 is moved away from the membrane structure 240, a narrow meniscus 320 forms between the conductive ring 310 and the first surface 210 of the membrane structure 240. Optionally, this separation distance, x, can be defined by a mechanical stop in the micro-droplet fluidic cell 300. The desired separation distance x may tolerate a range of values and depends on the desired application. The meniscus 320, or tapered portion of the micro-droplet 301 that may resemble an inverted neck, may minimize capacitive interaction with the second micro-droplet 231 that resides below the nanopore 150. In some embodiments, the analyte solution 230 is disposed within the conductive ring 310 a distance x from the first surface 210 of the membrane structure 240 sufficient to form a narrow meniscus 320.

The micro-droplet fluidic cell 300 is but an exemplary embodiment. Other embodiments of the micro-droplet fluidic cell 300 may be used.

Figure 4A:
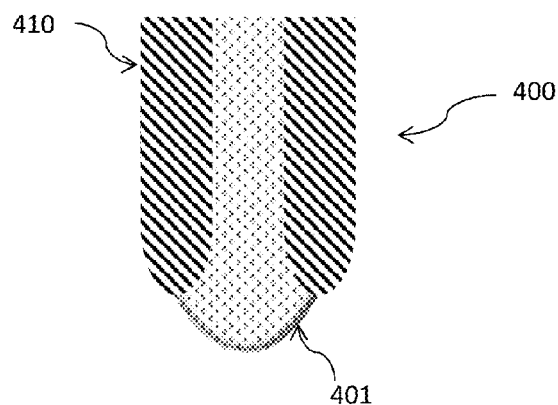
FIG. 4A illustrates a partially cut-away side view of an exemplary embodiment of a hollow needle wetted with an analyte solution before contacting the fluidic cell.
Figure 4B:
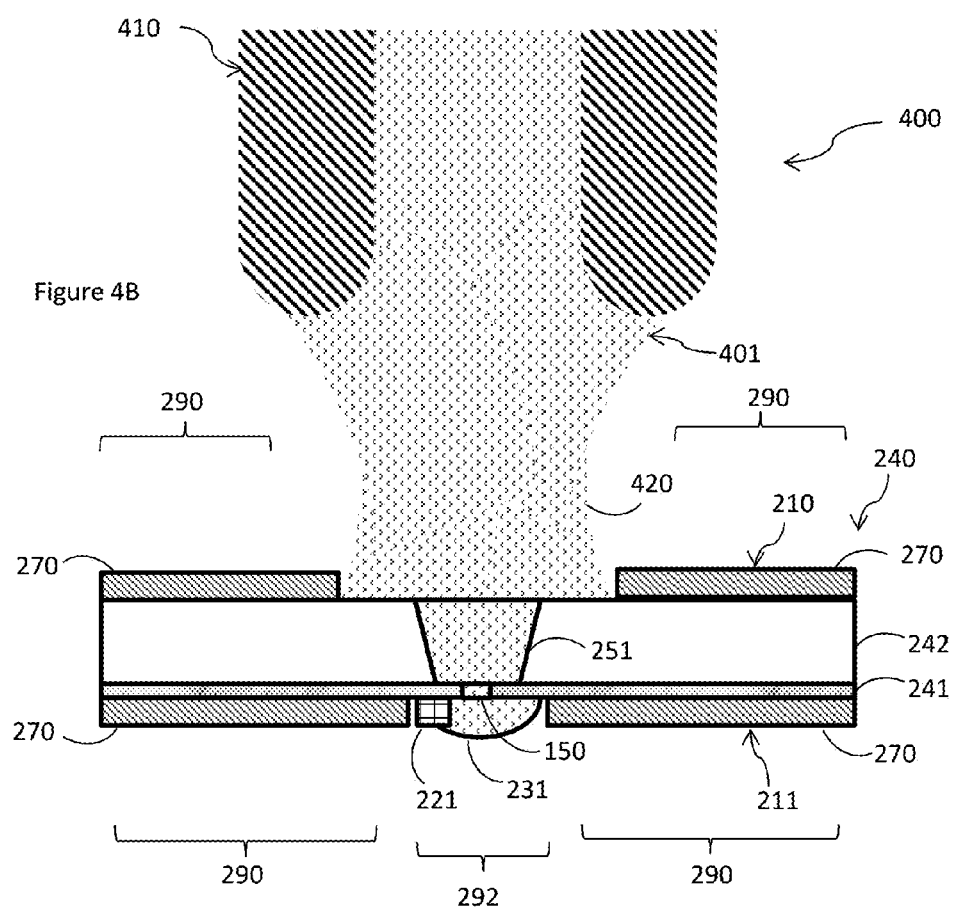
FIG. 4B illustrates a partially cut-away side view of an exemplary embodiment of a micro-droplet fluidic cell utilizing the hollow needle of FIG. 4A.

FIGS. 4A-B illustrate exemplary embodiments of a micro-droplet fluidic cell 400 utilizing a hollow needle 410 to form the micro-droplet 401. FIG. 4A shows a partially cut-away side view of the hollow needle 410 housing the analyte solution 230 before contacting the membrane structure 240. The hollow needle 410 forms a micro-droplet 401 on the needle tip. The hollow needle 410 provides a large surface contact area which may be beneficial for temperature-control and lowering electrode impedance.

FIG. 4B shows a partially cut-away side view of the hollow needle 410 contacting the membrane structure 240. Like the micro-droplet fluidic cell 300 of FIG. 3C, the membrane structure 240 does not use TSV 280 or a first electrode 220.

As the hollow needle 410 housing the micro-droplet 401 contacts the membrane structure 240, a meniscus 420 forms between the hollow needle 410 and the membrane structure 240. As in FIG. 3C, the narrow meniscus 420 may minimize capacitive interaction with the second micro-droplet 231 on the opposing side of the membrane structure 240. In one embodiment, the analyte solution 230 is disposed within the hollow needle 410, and a first end of the hollow needle 410 is positioned a distance from the first surface 210 of the membrane structure 240 sufficient to form a narrow meniscus 420 between the first end of the hollow needle 410 and the first surface 210 of the membrane structure 240.

The hollow needle 410 material is not limited and depends on the desired application. Non-limiting examples of suitable materials include metals, plastics, and semiconducting materials disclosed for the conductive ring 310. Optionally, the surface of the hollow needle 410 is coated or treated as described above for the conductive ring 310. To enable control of the micro-droplet 401 shape, the hollow needle 410 may be attached to a motorized micro-syringe.

The micro-droplet fluidic cell 400 is but an exemplary embodiment. Other embodiments of the micro-droplet fluidic cell 400 may be used.

Compared to the micro-droplet fluidic cell 200, which utilizes TSV 280 technology, micro-droplet fluidic cells 300 and 400 using the conductive ring 310 and the hollow needle 410 may use larger volumes of analyte solution 230. Larger volumes may simplify dispensing techniques.

In addition, the conductive ring 310 and the hollow needle 410 may be temperature-controlled. Control of analyte temperature during analysis may be beneficial in a variety of chemical and biochemical studies. Precise control of the analyte temperature near the phase transition temperature may allow for viscosity control during analysis. In some instances, viscous solutions may be desired because they may dampen thermally induced (Brownian) motion of biological molecules, which can lead to improvements in signal-to-noise ratios.

The micro-droplet fluidic cells described above may be used in multiple arrays. For example, a micro-droplet fluidic cell array may have a plurality of micro-droplet fluidic cells using any of the above described embodiments (TSV technology, conductive rings, and/or hollow needles). The conductive rings 310 and hollow needles 410 may be temperature-controlled so that each individual micro-droplet maintains a different temperature. However, the plurality of micro-droplets may be maintained at the same temperature. Arrays of heating elements may be used to moderate the temperature.

A plurality of conductive rings 310 may be injection molded or etched from thin metal sheets. Because the second electrode 221 is still individually controllable, the conductive rings 310 may share the same electrical potential. A plurality of hollow needles 410 may be made from a common material that dispenses the analyte solution 230 into an array of nanopores 150. However, a plurality of individual hollow needles 410 may be used.

Figure 5:
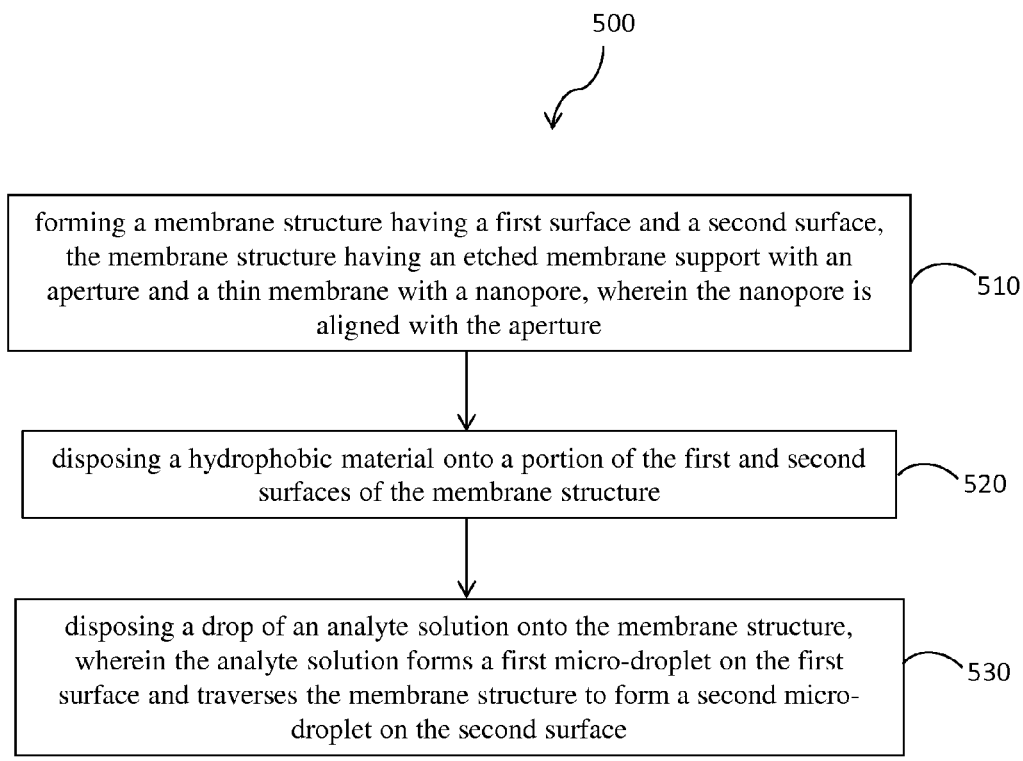
FIG. 5 illustrates a block diagram of an exemplary method for fast ionic current detection using the micro-droplet fluidic cell of FIG. 2, 3C, or 4B.

FIG. 5 illustrates a block diagram of an exemplary method 500 for fast ionic current detection. In block 510, the method includes forming a membrane structure having a first surface and a second surface. The membrane structure has an etched membrane support with an aperture and a thin membrane with a nanopore, and the nanopore is aligned with the aperture. In block 520, a hydrophobic material is disposed onto a portion of the first and second surfaces of the membrane structure. In block 530, a drop of an analyte solution is disposed onto the membrane structure. The analyte solution forms a first micro-droplet on the first surface and traverses the membrane structure to form a second micro-droplet on the second surface. The method 500 is but an exemplary embodiment. Other embodiments of micro-droplet fluidic cell 500 may be used.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A micro-droplet fluidic cell comprising:
   a membrane structure configured to reduce parasitic capacitance, having:
     an etched membrane support with an aperture, and
     a thin membrane with a nanopore arranged on a bottom surface of the etched membrane support, the thin membrane being thinner than the etched membrane support;
   the nanopore being aligned with the aperture, the aperture having a diameter in a range from about 100 nanometers to about 100 micrometers, the nanopore having a diameter in a range from about 1 to about 900 nanometers, and the diameter of the nanopore being smaller than the aperture;
   a hydrophobic material disposed onto a top surface of the etched membrane support, the hydrophobic material having an opening around the aperture such that the etched membrane support is exposed around the aperture and the opening around the aperture is hydrophilic;
   the hydrophobic material disposed onto a bottom surface of the thin membrane, the hydrophobic material having an opening around the nanopore such that the thin membrane is exposed around the nanopore and the opening around the nanopore is hydrophilic, and the opening around the nanopore being smaller than the opening around the aperture; and
   an analyte solution disposed onto the opening around the aperture and the exposed top surface of the etched membrane support, the analyte solution forming a first micro-droplet that traverses the aperture and the nanopore to form a second micro-droplet exiting through the nanopore, the second micro-droplet having a diameter that is smaller than the first microdroplet;
   wherein the opening of the hydrophobic material on the top surface of the etched membrane support is larger than the opening of the hydrophobic material on the bottom surface of the thin membrane.

2. A combination of the micro-droplet fluidic cell of claim 1, and a conductive ring which brings the analyte solution into contact with the membrane structure.

3. The micro-droplet fluidic cell of claim 1, wherein the micro-droplet further comprises a narrow meniscus between the micro-droplet and the first surface of the membrane structure.

4. A combination of the micro-droplet fluidic cell of claim 3, and a conductive ring that is temperature-controlled.

5. A combination of the micro-droplet fluidic cell of claim 1, and a hollow needle forming the micro-droplet.

6. The combination of the micro-droplet fluidic cell and the hollow needle of claim 5, wherein the hollow needle is temperature-controlled.

7. A micro-fluidic cell array comprising a plurality of micro-droplet fluidic cells of claim 1.

8. A combination of the micro-droplet fluidic cell of claim 1 and a conductive ring, wherein the analyte solution is disposed within the conductive ring positioned a distance from the first surface of the membrane structure sufficient to form a narrow meniscus between the conductive ring and the first surface.

9. A combination of the micro-droplet fluidic cell of claim 1 and a hollow needle, wherein the analyte solution is disposed within the hollow needle and a first end of the hollow needle is positioned a distance from the first surface of the membrane structure sufficient to form a narrow meniscus between the first end of the hollow needle and the first surface of the membrane structure.

10. A method for fast ionic current detection, the method comprising:
    forming a micro-droplet fluidic cell, comprising:
        a membrane structure comprising;
            an etched membrane support comprising an aperture, and
            a thin membrane comprising a nanopore arranged on a bottom surface of the etched membrane support, the thin membrane being thinner than the etched membrane support,
            the nanopore being aligned with the aperture, the aperture having a diameter in a range from about 100 nanometers to about 100 micrometers, the nanopore having a diameter in a range from about 1 to about 900 nanometers, and the diameter of the nanopore being smaller than the aperture;
    disposing a hydrophobic material onto a top surface of the etched membrane support, the hydrophobic material having an opening around the aperture such that the etched membrane support is exposed around the aperture and the opening around the aperture is hydrophilic;
    disposing the hydrophobic material onto a bottom surface of the thin membrane, the hydrophobic material having an opening around the nanopore such that the thin membrane is exposed around the nanopore and the opening around the nanopore is hydrophilic, and the opening around the nanopore being smaller than the opening around the aperture; and
    reducing parasitic capacitance by disposing a drop of an analyte solution onto the opening around the aperture of the membrane structure and the exposed top surface of the etched membrane support, the analyte solution forming a first micro-droplet that traverses the aperture and the nanopore to form a second micro-droplet exiting through the nanopore, the second micro-droplet having a diameter that is smaller than the first micro-droplet;
    wherein the opening of the hydrophobic material on the top surface of the etched membrane support is larger than the opening of the hydrophobic material on the bottom surface of the thin membrane.

11. The method of claim 10, further comprising wetting the analyte solution with a conductive ring and touching the analyte solution to the membrane structure.

12. The method of claim 10, further comprising using a hollow needle or a micro-pipette to dispose the drop of the analyte solution onto the membrane structure.

13. The method of claim 10, further comprising measuring an ionic current to detect a molecule within the analyte solution passing through the nanopore.

14. The method of claim 10, further comprising applying a pressure differential across the membrane structure, the nanopore, or both the membrane structure and the nanopore.

* * * * *